United States Patent [19]

Dotta

[11] 4,235,337

[45] Nov. 25, 1980

[54] RAPIDLY OPENING SEALED PACKAGE FOR WOUND DRESSING ADHESIVE TAPE

[76] Inventor: Angelo Dotta, Via Altagella 10,, Bologna, Italy

[21] Appl. No.: 972,514

[22] Filed: Dec. 22, 1978

[30] Foreign Application Priority Data

Jan. 6, 1978 [IT] Italy .................. 12409 A/78

[51] Int. Cl.³ .............. A61F 13/02; A61L 15/06
[52] U.S. Cl. ................. 206/441; 128/155
[58] Field of Search ........... 206/441, 440, 438; 128/155, 156

[56] References Cited

U.S. PATENT DOCUMENTS

| | | | |
|---|---|---|---|
| 3,018,881 | 1/1962 | Wall | 206/441 |
| 3,899,077 | 8/1975 | Spiegelberg | 206/441 |

FOREIGN PATENT DOCUMENTS 593699  3/1960  Canada .................. 128/156

Primary Examiner—Herbert F. Ross

[57] ABSTRACT

A rapidly opening sealed package for wound dressing adhesive tape comprising an adhesive support carrying a wound dressing pad covered endwise by a pair of protective films attached to a pair of outer sheaths so that by pulling the outer sheaths apart the protecting films will move therewith to separate centrally and uncover the wound dressing pad.

11 Claims, 7 Drawing Figures

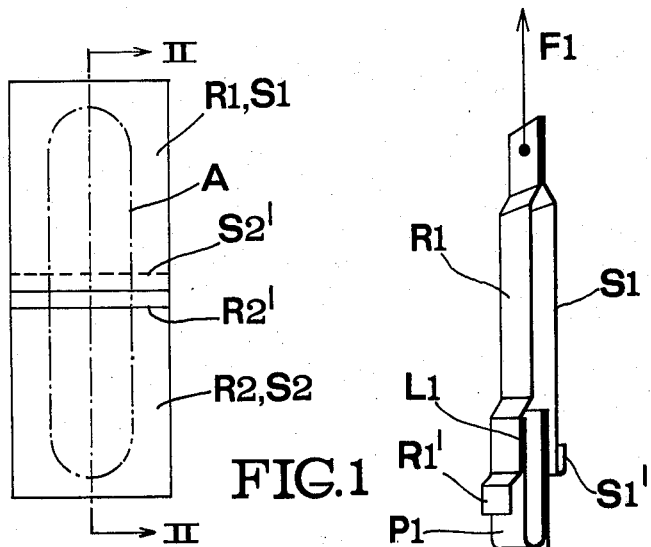
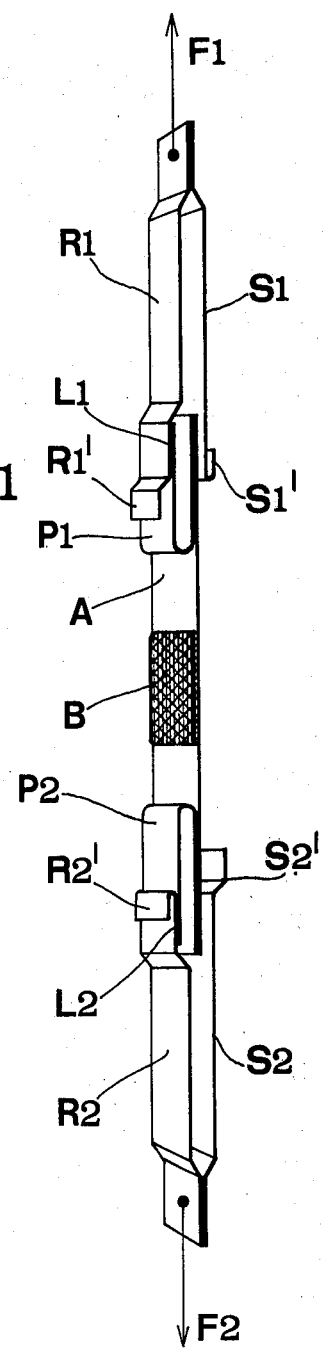
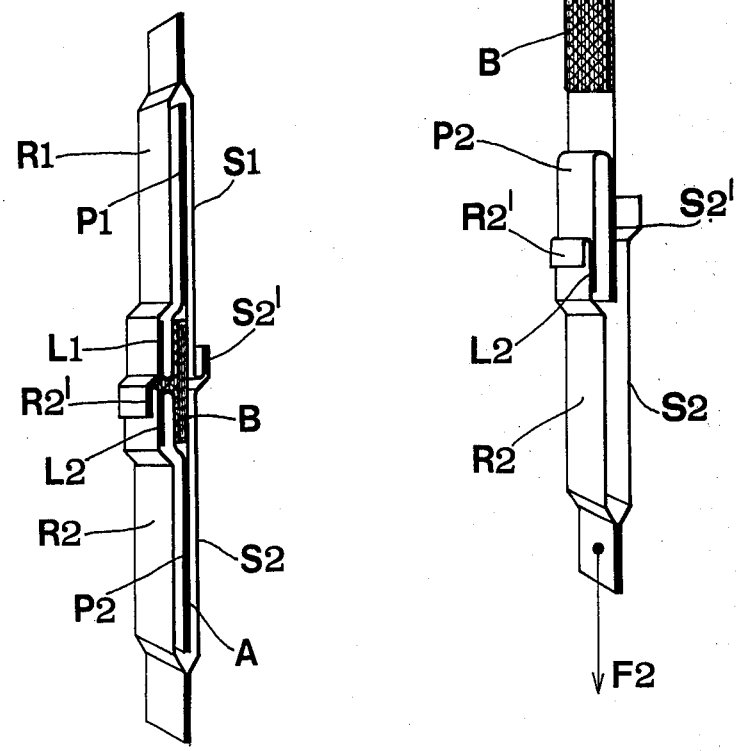
FIG.1
FIG.2
FIG.3

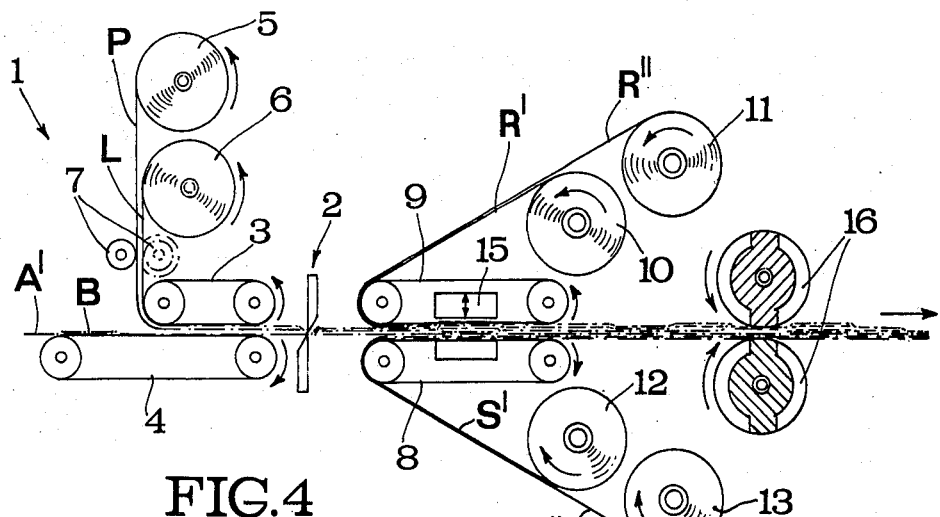
FIG.4
FIG.5
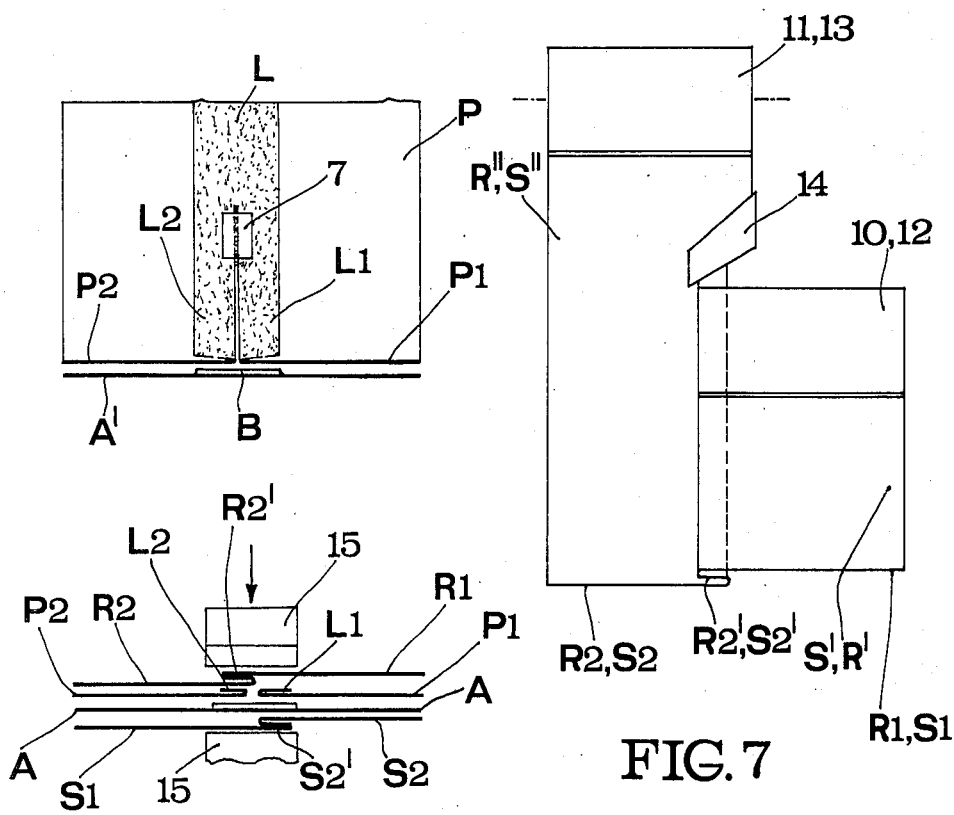
FIG.6
FIG.7

RAPIDLY OPENING SEALED PACKAGE FOR WOUND DRESSING ADHESIVE TAPE

This invention relates to a rapidly opening sterilizable sealed package for adhesive tape for wound dressing and the like.

The known sterilized sealed packages for wound dressing adhesive tape usually require a delicate operation for opening them, often involving a risk of touching the wound dressing tape with the fingers.

It is an object of the present invention to eliminate this disadvantage and to provide a sterilizable sealed package for adhesive tape that can be rapidly opened without any risk of being touched with the fingers by the person opening it.

This object is achieved according to the present invention by providing a rapidly opening sterilizable sealed package for wound dressing adhesive tape which comprises:

an adhesive support carrying a wound dressing pad on one side thereof;

a pair of protecting films applied to one side of said adhesive support in opposed positions along the length thereof so as to meet substantially centrally over said wound dressing pad where they are separated from one another and have folded-back laps; and a pair of outer sheaths sealingly attached to said pair of protecting films and having folded-back portions adhesively attached to said folded-back laps of said protecting films and separably adhesively attached to one another in a position adjacent said wound dressing pad, said outer sheaths having a pair of gripping extensions at opposed ends thereof so that by gripping said extensions and pulling them apart in opposite directions said outer sheaths will separate centrally and in their outward movement away from one another will also move said protecting films outwardly to uncover said wound dressing pad.

In this manner the wound dressing pad can be rapidly and conveniently uncovered without any risk of ever touching it with the fingers.

A preferred embodiment of the invention will now be described by way of example and with reference to the accompanying drawings, in which:

FIG. 1 is a schematic plan view of a wound dressing adhesive tape package according to the invention in the closed position;

FIG. 2 is a perspective view of the same package in a section taken along the line II—II of FIG. 1;

FIG. 3 is a perspective view as in FIG. 2, showing the package as it is being opened;

FIG. 4 is a schematic side view of an apparatus for making the adhesive tape package shown in FIGS. 1 to 3;

FIG. 5 is a front elevational view of the portion of the apparatus of FIG. 4 where the protecting films are applied to the adhesive tape;

FIG. 6 is a front view of the portion of the apparatus where the outer sheaths are secured to predetermined portions of the adhesive tape protecting films, and FIG. 7 is a schematic bottom plan view of the portion of the apparatus where part of the outer sheaths is prepared.

Referring first to FIGS. 1 and 2, indicated by A is an adhesive support to the central portion of which a sterile wound dressing pad B is secured in known manner. A pair of protecting films P1 and P2, respectively, made of plastics material in the conventional manner, is applied to the adhesive support A so as to meet along the transverse center line thereof where according to the invention they are provided with laps L1, L2 folded back over the protecting films P1, P2.

The dressing pad with its adhesive support is then placed in a package which may be made, for example, of paper appropriately treated with some suitable adhesive at least on its inside surface, i.e. that located within the package when it is closed. This package comprises portions R1, R2 located on the protecting films P1, P2 as well as portions S1, S2 located below the adhesive support A, the size of the package being selected to be greater than that of the dressing pad B and its adhesive support A so as to enclose them sealingly on all sides in a suitably dimensioned bag.

Each of the portions R2 and S2 of the package has at its end facing the transverse center line of the dressing pad a folded-back portion R2' and S2', respectively, on which the gummed inner surface of the respective portion R2 and S2 is turned outside and thus can be sealingly attached to the adjacent end R1' and S1' of the portions R1 and S1, respectively, of the package.

The laps L1, L2 of the protecting films P1, P2 are coated with some suitable adhesive on their surfaces located adjacent the package portions R1, R2 and are firmly secured to the latter by such adhesive.

To open this adhesive tape package it is sufficient to grip the outer ends of the package portions R1 and R2 and pull them apart as indicated by the arrows F1 and F2. Under the effect of this pulling action the package will be separated in its center into two portions or hulls formed by the parts R1, S1 and R2, S2, respectively, which will separate from one another in the central portion where they were previously adhesively attached and will uncover the wound dressing pad B and its adhesive support A because the package portions R2 and R1 are firmly secured to the protecting films P1 and P2 through the laps L1, L2 and thus will progressively detach also the protecting films P1, P2 as the package portions R2 and R1 move outwardly.

It will thus be evident that, as the package is thus gradually opened, the wound dressing pad can be applied to a wound without ever having to touch it with the fingers. It is also evident that the operations of opening the package and applying the wound dressing pad to a wound are much more convenient and rapid than with a conventional wound dressing adhesive tape.

Instead of meeting with the laps L1 and L2 over the wound dressing pad B, the protecting films P1, P2 may also meet over some other free portion of the adhesive support A to avoid excessive thickening in the central portion of the package. For the same purpose also the outer package portions R1, R2 and S1, S2, respectively, may meet in some other position outside the wound dressing pad B so that their respective connecting lines will never overlap.

Instead of being made of paper treated with some adhesive, the outer package may also be made of other appropriate material, for example, plasticized paper or thermoplastic film material, provided that it ensures complete and reliable sealing of the wound dressing pad. Also sealing of the laps L1, L2 to the package portions R1, R2 and reciprocal sealing between the components of the outer package can be obtained by gumming one or both of the adjacent surfaces to be connected. For such gumming natural or permanent adhesives may be used or substances that become adhesive by subsequent application of pressure, heat or the like. If the various parts making up the package permit it, sealing may also be obtained without adding any particular sealing material. This would particularly be the case if the package was entirely or partly made of thermoplastic film material.

The laps L1, L2 may be formed by extensions of the protecting films P1, P2 or by separate portions attached thereto.

Finally, to facilitate the separation of the outer package portions R1, S1 from the outer package portions R2, S2, an easily detachable adhesive connection may be provided there between, i.e. a connection in which the connected portions overlap in a relatively small area, using an adhesive element that is well sealing but little resistant to traction. Alternatively, the portions R1, R2 and S1, S2, respectively, may be made of a single strip having a weakened central portion provided for example, by transverse indentations or chemical substances. If necessary, an adhesive sealing element may be applied to the inner surface of the outer package portions R1, R2 and secured to the folded-back laps L1, L2.

The wound dressing adhesive tape package thus described may be made by any conventional means and process. However, merely by way of example, a preferred apparatus for making it will now be described with reference to FIGS. 4 to 7.

As shown in FIG. 4, in a working station 1 the continuous adhesive support A' with the wound dressing pads B placed at equal distances thereon is provided with the protecting films P1 and P2 which may be supplied, for example, by opposed synchronized conveyor belts 3 and 4. Then the adhesive support A' is cut transversely in a cutting station 2 to form the separate adhesive tapes each provided with a wound dressing pad B. The protecting films P1 and P2 may be produced from a single film P unwound from a reel 5. A second film of reduced width L is unwound from a second reel 6 and placed longitudinally in the central area of the film P on the upper surface thereof, i.e. the upper surface as the package is opened. The upper surface of the second film L is coated with adhesive for connecting it to the inner surface of the outer package, as previously described. Before the films P and L reach the upper portion of the adhesive support A', they are subjected to the action of continuously or intermittently operating means 7 (see also FIG. 5) for double sealing and cnetrally cutting the films so that at the outlet of this means and before the film P is applied to the adhesive support A', the film P will be divided into two portions which provide the protecting films P1 and P2 to the adjacent ends of which are sealed overlapping equal portions of the film L forming the laps L1, L2 already provided with properties facilitating their connection to the outer package, as will be described hereinafter.

In another station following the cutting station 2, the wound dressing pads already provided with the protecting films P1, P2 and associated laps L1, L2, and appropriately spaced from one another by a predetermined amount, are provided with the outer package, for example, by a further pair of opposed and synchronized conveyor belts 8 and 9. The portions R1, R2 and S1, S2 forming the outer package may be supplied by respective appropriately pretreated bands R', R" and S', S" each unwound from a reel 10, 11 and 12, 13, respectively. FIG. 7 shows a folding device 14 in association with a pair of said reels for folding one of these bands in an area R2' or S2' overlying or underlying the other band R1 or S1. The folding device 14 may also be replaced by other appropriate conventional means. Further, means, not shown, may be provided to exert the necessary pressure for sealing the overlapping portions of the outer package before they reach the conveyor belts 8, 9 for application to the wound dressing pads. Alternatively, this pressure sealing operation or any other suitable sealing operation may be carried out separately at a later stage.

As shown particularly in FIG. 6, the station for application of the outer package in the illustrated embodiment comprises means 15 for exerting pressure in the intermediate area of the outer package for securing the outer package portions R1 and R2 to the laps L1, L2 of the protecting films P1 and P2.

The outer package may also be applied in a different order of working phases; for example, first the upper covering formed of the package portions R1 and R2 and then the lower covering formed by the portions S1 and S2 may be secured in position.

In another station following that of application of the outer package, continuously or intermittently operating means, for example, profiled synchronized rollers 16, are provided to exert pressure on the outer package in the area outwardly of the wound dressing pads to reciprocally connect and seal the various parts forming the package.

In the described apparatus it is assumed that at least the surfaces of the bands R1, R2 and S1, S2 remaining inside the package as well as the visible surfaces of the laps L1, L2 are previously treated with adhesive of the type known under the trade name "Cosil" or the like, i.e. materials that can be made adhesive subsequently by exerting pressure thereon. Alternatively, at least for sealing the laps L1, L2 to the outer package portions R1, R2, any suitable adhesive may be used that can be spread on a central strip of the outer package portions R1, R2 after they have been joined and before they are placed on the adhesive support where the central strip coated with adhesive is applied and sealed to the laps L1, L2.

Although a preferred embodiment of the wound dressing adhesive tape according to the invention and an apparatus for making it have thus been described by way of example, it is to be understood that numerous changes and modifications obvious to one skilled in the art may be made both in the apparatus and the adhesive tape without departing from the scope of the invention as defined by the appended claims.

I claim:

1. A rapidly opening sterilizable sealed package for wound dressing adhesive tape comprising:
   an unfolded adhesive support carrying a wound dressing pad midway on one side thereof;
   a pair of protecting films applied to one side of said adhesive support in opposed positions along the length thereof so as to meet substantially centrally over said wound dressing pad where they are separated from one another and have folded-back laps; and
   a first pair of outer sheaths overlying and attached to said pair of protecting films, at least one of which has a folded-back portion adhesively attached to one of said folded-back laps of said protecting films and the other of which is adhesively attached to the folded back lap of the other of said protecting films, said sheaths being separably adhesively attached to one another in a position adjacent and on said one side of said wound dressing pad, a second pair of outer sheaths coextensive with said first pair of outer sheaths on the other opposite side of said adhesive support, said second pair of outer sheaths being firmly secured to said first pair of outer sheaths at respective free ends thereof remote from said wound dressing pad so as to form gripping extensons, which when pulled apart in opposite directions, cause said outer sheaths to separate centrally and in their outward movement away from one another will also move said protecting films outwardly to uncover said wound dressing pad.

2. A rapidly opening sterilizable sealed package as claimed in claim 1, wherein said first and second pairs of outer sheaths are formed by four strips of material extending longitudinally of said package one above and one below said wound dressing pad, said pair extending above said wound dressing pad having a portion coated with adhesive on their ends and sides directed toward the inside of the package, and being sealed together peripherally of said wound dressing pad, each of said four strips having a folded strip having a folded-back portion also coated with adhesive facing a similar folded-back portion coated with adhesive on the adjacent strip in the longitudinal direction of said package, said adhesive folded-back portions being sealed together with slight overlap so as to offer little resistance to pulling them apart in the longitudinal direction of said package, said resistance being less than the resistance offered by said portion coated with adhesive of said strips located above said wound dressing pad.

3. A rapidly opening sterilizable sealed package as claimed in claim 1, wherein said first and second pair of outer sheaths are formed by two strips of material coated with adhesive at their inner ends on their sides directed toward the inside of the package, placed one above and one below said wound dressing pad, sealed together peripherally of said wound dressing pad and having an intermediate weakened portion.

4. A rapidly opening sterilizable sealed package as claimed in claim 3, wherein a strip of sealing adhesive material is applied inwardly of said weakened portion for connection to said folded-back laps of said protecting films.

5. A rapidly opening sterilizable sealed package as claimed in claim 1, wherein said folded-back laps of said protecting films are formed by extensions of the latter.

6. A rapidly opening sterilizable sealed package as claimed in claim 1, wherein said folded-back laps of said protecting films are formed by separate elements applied to said protecting films.

7. A rapidly opening sterilizable sealed package as claimed in claim 1, wherein said folded-back laps of said protecting films are made of one strip of material having applied to the central portion thereof another narrower strip, these two strips being connected to one another by a pair of adjacent parallel transverse welding seams and then cut transversely in the area between said welding seams so as to form said folded-back laps on said protecting films.

8. A rapidly opening sterilizable sealed package as claimed in claim 1, wherein said folded-back laps of said protecting films are sealed to the adjacent portions of said outer sheaths by adhesive.

9. A rapidly opening sterilizable sealed package as claimed in claim 1, wherein said folded-back laps of said protecting films are sealed to the adjacent portions of said outer sheaths by a material made adhesive by exerting pressure thereon.

10. A rapidly opening sterilizable sealed package as claimed in claim 1, wherein said folded-back laps of said protecting films are sealed to the adjacent portions of said outer sheaths by a material made adhesive under the influence of heat.

11. A rapidly opening sterilizable sealed package as claimed in claim 1, wherein the central adjacent ends of said protecting films may be secured to the adjacent portions of said first pair of outer sheaths by any conventional process compatible with the material of the parts to be connected and ensuring adequate resistance of the thus connected parts to a force tending to pull those parts apart.

* * * * *